US00PP09097P

United States Patent [19]

Marciel et al.

[11] Patent Number: Plant 9,097

[45] Date of Patent: Apr. 4, 1995

[54] HYBRID TEA ROSE PLANT NAMED DEVPAJARO

[75] Inventors: Stanley G. Marciel; Jeanne A. Marciel, both of Aptos, Calif.

[73] Assignee: DeVor Nurseries, Inc., Freedom, Calif.

[21] Appl. No.: 217,970

[22] Filed: Mar. 25, 1994

[51] Int. Cl.[6] ..... A01H 5/00

[52] U.S. Cl. ..... Plt./20

[58] Field of Search ..... Plt. 11, 12, 17, 18, Plt. 20

*Primary Examiner*—Howard J. Locker

*Attorney, Agent, or Firm*—Christie, Parker & Hale

[57] ABSTRACT

A new hybrid tea rose plant producing red orange flowers.

1 Drawing Sheet

SUMMARY OF THE INVENTION

The present invention relates to a new and distinct variety of rose plant of the hybrid tea rose class which was originated by crossing as seed parent the variety known as 'Jacqueline', (U.S. Plant Pat. No. 2,183) and as pollen parent the variety known as 'Prominent', (U.S. Plant Pat. No. 3,380). The varietal denomination of this new rose is 'Devpajaro'.

Among the novel characteristics possessed by this new variety which distinguish it from its parents and all other varieties of which I am aware are its attractive large red orange flowers suitable for growing under glass for cut flower production.

Asexual reproduction by budding of the new variety as performed in Watsonville, Calif. shows that the foregoing and other distinguishing characteristics come true to form and are established and transmitted through succeeding propagations.

COMPARISON WITH PARENTS

The new variety produces large flowers on sturdy stems. Flowers produced by both parents are orange, whereas 'Devpajaro' flowers have more red/orange coloration and are larger.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Jacqueline' (U.S. Plant Pat. No. 2,183).

*Pollen parent.*—'Prominent' (U.S. Plant Pat. No. 3,380).

Class: Hybrid tea.

The following is a detailed description of my new variety, of new specimens grown under glass in Watsonville, Calif. in the month of September. The color terminology used is in accordance with the Royal Horticultural Society Colour Chart (RHSCC) and refers to plate numbers in the aforementioned color chart. Phenotypic expression may vary depending on light, environmental and cultural conditions.

FLOWER

Blooming habit: Continuous.

A. Bud:

(1) *Size.*—Medium.

(2) *Form.*—Slender and tapering.

(3) *Color.*—Before sepals divide, near 61B.

(4) *Sepals.*—Longer than bud, foliaceous, color near 143B.

(5) *Peduncle.*—Length: About 6–12 cm. Aspect: Slightly curved, with some prickles. Strength: Heavy. Color: Near 147C to B.

(6) *Bracts.*—None.

B. Bloom:

(1) *Size.*—Average size when fully expanded — about 10–11 cm.

(2) *Borne.*—Singly, one to a stem.

(3) *Form.*—Imbricated, high-centered at first.

(4) *Petalage.*—Number of petals under normal conditions — about 27.

(5) *Color.*—($\frac{1}{3}$ to $\frac{1}{2}$ open): Outer petals — Top surface Top: Red 46B, Center: Red 44B, Base: Yellow 11D. Under surface Top: Red 50A. Center: Red 46C. Base: Yellow 11D. Base of petals (point of attachment) Yellow 11D. General tonality from a distance Red/Orange. (Fully opened): Outer petals — Top surface Top: Red 45B. Center: Red 43B. Base: Yellow 8D. Undersurface Top: Red 52A. Center: Red 43B. Base: Yellow 4D. Inner petals — Top surface Top: Red 46C. Center: Red 43B. Base: Yellow 11D. Undersurface Top: Red 50A. Center: Red 52A. Base: Yellow 11D. Base of petals (point of attachment) Yellow 11D. General tonality from a distance Red/Orange. Color of bloom upon aging deepens slightly to Red Group 44A on the petal top surface and Red Group 50A on the petal undersurface, and the general tonality at a distance is red/orange.

C. Petals:

(1) *Texture.*—Thick.

(2) *Appearance.*—Inside velvety and outside smooth.

(3) *Form.*—Curled.

(4) *Arrangement.*—Regularly arranged, imbricated.

(5) *Petaloids.*—Few, about 4–5.

(6) *Fragrance.*—Slight.

(7) *Lasting quality.*—8–10 days as cut flower; petals hold well for greenhouse variety.

(8) *Persistence.*—Drop off cleanly.

REPRODUCTIVE ORGANS

A. Stamens:
(1) *Arrangement.*—Regularly arranged.
(2) *Anthers.*—Color near 167B.
(3) *Filaments.*—Near 64A.
(4) *Pollen.*—Color near 186B.
(5) *Stamens.*—Top-near 64A; bottom-near 167B.

B. Pistils
(1) *Styles.*—Bunched, uneven length.
(2) *Stigmas.*—Color near 18C.

C. Characteristics of hips: Not observed.

PLANT

A. Form: Upright, compact.
B. Growth: Very vigorous, uniform branching.
C. Foliage: Compound 3, 5 and 7 leaflets.
(1) *Size.*—Large.
(2) *Quantity.*—Abundant.
(3) *Color.*—New foliage — upper side near 146A, underside near 177B; old foliage — upper side near 137A, underside near 148B.
(4) *Shape.*—Oblong.
(5) *Texture.*—Smooth, semi-glossy, underside dull.
(6) *Edge.*—Serrate.
(7) *Serration.*—Serrate.
(8) *Leaf stem.*—Color — medium green.
(9) *Stipules.*—Medium length, bearded.

(10) *Rachis.*—Smooth.
(11) *Petioles.*—Top near 137A, underside near 144A.
(12) *Auricle.*—Very long — about 1 cm, pointed, curving slightly outward.
(13) *Resistance to disease.*—Under greenhouse conditions no rust and blackspot; average resistance to mildew.

D. Wood
(1) *New wood.*—Near 146A, smooth.
(2) *Old wood.*—Near 144A, smooth.

E. Flower stem: About 75-80 cm from last cut.

F. Thorns:
*Quantity.*—On main stalk, few; on laterals from stalk, few.
*Form.*—Pointed, slightly curved downward, wide base.
*Length.*—Long.
*Color.*—Near 182A at base, tip near 191B.
*Position.*—Irregular.
*Prickles.*—Few.

F. Winter hardiness: Greenhouse variety; wintered well in California.

I claim:

1. A new and distinct variety of rose plant of the hybrid tea rose class, substantially as herein shown and described.

* * * * *

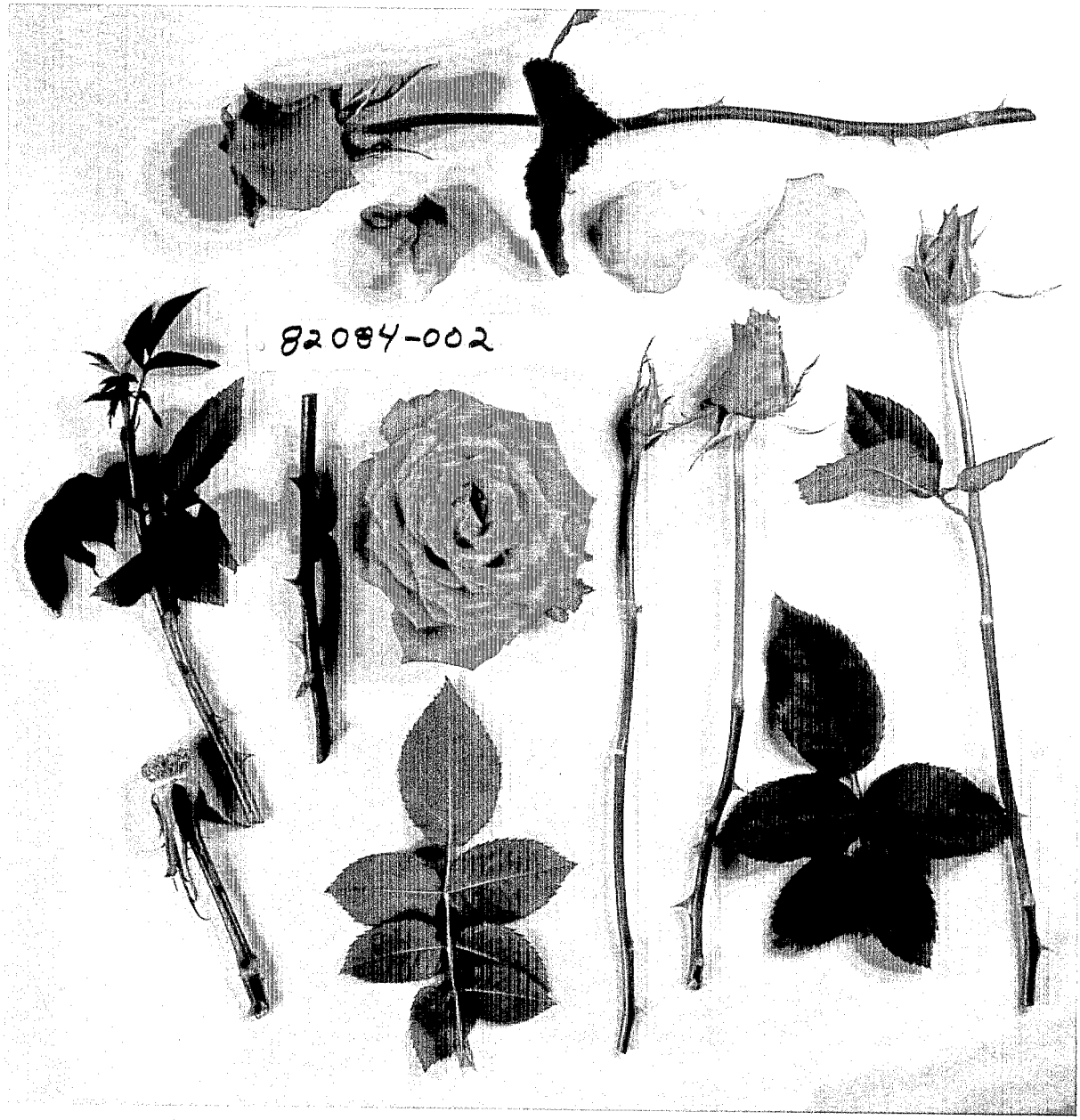
82084-002

UNITED STATES PATENT AND TRADEMARK OFFICE

CERTIFICATE OF CORRECTION

PATENT NO. : Plant 9,097

DATED : April 4, 1995

INVENTOR(S) : Stanley G. Marciel; Jeanne A. Marciel

It is certified that error appears in the above-indentified patent and that said Letters Patent is hereby corrected as shown below:

On the Title Page, Item 56, after Item 58 insert
-- [56] References Cited
U.S. PATENT DOCUMENTS
P.P. 7,390 12/1990 Meilland....Plt/20 --

Signed and Sealed this

Fifth Day of March, 1996

*Attest:*

*Attesting Officer*

BRUCE LEHMAN

*Commissioner of Patents and Trademarks*